United States Patent [19]
Handanyan et al.

[11] Patent Number: 5,763,454
[45] Date of Patent: Jun. 9, 1998

[54] CRYSTAL FORM OF ANHYDROUS 7-([1α,5α,6α]-6-AMINO-3-AZABICYCLO[3.1.0]HEX-3-YL)-6-FLUORO-1-(2,4-DIFLUOROPHENYL)-1,4-DIHYDRO-4-OXO-1,8 NAPHTHYRIDINE-3-CARBOXYLIC ACID, METHANESSULFONIC ACID SALT

[75] Inventors: Lynne A. Handanyan; Thomas A. Morris; Robert L. Hendrickson; Phillip J. Johnson; Timothy Norris, all of New York, N.Y.

[73] Assignee: Pfizer, Inc., New York, N.Y.

[21] Appl. No.: 849,300

[22] PCT Filed: Jun. 6, 1995

[86] PCT No.: PCT/US95/07211

§ 371 Date: May 21, 1997

§ 102(e) Date: May 21, 1997

[87] PCT Pub. No.: WO96/39406

PCT Pub. Date: Dec. 12, 1996

[51] Int. Cl.⁶ .......... A61K 31/435; A61K 31/47; C07D 471/04; C07D 215/312
[52] U.S. Cl. .......... 514/300; 514/312; 514/19; 546/123; 546/156
[58] Field of Search .......... 514/300, 312; 546/123, 156

[56] References Cited

U.S. PATENT DOCUMENTS 5,164,402  11/1992  Brighty .......... 514/300
5,229,396  7/1993  Brighty .......... 514/300

FOREIGN PATENT DOCUMENTS 413455    of 0000   European Pat. Off.
2289674   11/1995   United Kingdom .......... C07D 471/04
9519361   7/1995    WIPO Primary Examiner—José G. Dees
Assistant Examiner—Sabiha N. Qazi
Attorney, Agent, or Firm—Peter C. Richardson; Paul H. Ginsburg; Gezina Holtrust

[57] ABSTRACT

The anhydrate of 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt has advantageous stability for formulation as an antibacterial agent.

4 Claims, No Drawings

CRYSTAL FORM OF ANHYDROUS 7-([1α,5α,6α]-6-AMINO-3-AZABICYCLO[3.1.0]HEX-3-YL)-6-FLUORO-1-(2,4-DIFLUOROPHENYL)-1,4-DIHYDRO-4-OXO-1,8 NAPHTHYRIDINE-3-CARBOXYLIC ACID, METHANESSULFONIC ACID SALT

BACKGROUND OF THE INVENTION

The invention is directed to a novel crystal form of anhydrous 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt, a method of using said compound in the treatment of a bacterial infection in mammals, especially humans, and to pharmaceutical compositions useful therefor.

U.S. Pat. No. 5,229,396, which is incorporated herein by reference, discloses 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt of the formula

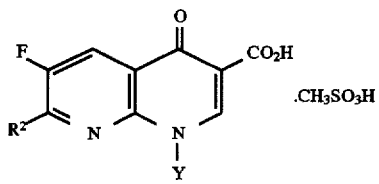

I wherein Y is o,p-difluorophenyl and $R^2$ is

II having antibacterial activity.

SUMMARY OF THE INVENTION

The invention is directed to a novel crystal form of anhydrous 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt which possesses valuable and nonobvious properties. Since the anhydrate is substantially hydrophobically stable, formulation problems of the active ingredient during tableting or capsulation operations are alleviated.

DETAILED DESCRIPTION OF THE INVENTION

The 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt referred to in U.S. Pat. No. 5,229,396 characterized by the major peaks in the following X-ray powder diffraction pattern

| Peak no. | 1 | 2 | 3 | 4 | 5 | 6 | 7 | 8 |
|---|---|---|---|---|---|---|---|---|
| 2θ(°) Cu | 4.7 | 9.4 | 12.4 | 13.1 | 13.6 | 14.2 | 17.0 | 17.9 |
| d space | 18.7 | 9.4 | 7.1 | 6.7 | 6.5 | 6.3 | 5.2 | 5.0 |

| Peak no. | 9 | 10 | 11 | 12 | 12 | 14 | 15 |
|---|---|---|---|---|---|---|---|
| 2θ(°) Cu | 18.7 | 21.0 | 22.0 | 24.2 | 24.2 | 26.6 | 27.2 |
| d space | 4.7 | 42 | 4.0 | 3.7 | 3.7 | 3.5 | 3.3 | is substantially hygroscopic and can pick up water from the atmosphere to form a monohydrate. The monohydrate is characterized by the major peaks in the following X-ray powder diffraction pattern The novel crystal form of 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt (hereinafter "the anhydrate") is hydrophobically stable and characterized by the major peaks in the following X-ray powder diffraction pattern.

| Peak no. | 1 | 2 | 3 | 4 | 5 | 6 | 7 | 8 |
|---|---|---|---|---|---|---|---|---|
| 2θ(°) Cu | 4.5 | 7.7 | 9.1 | 13.6 | 15.0 | 18.2 | 18.6 | 22.8 |
| d space | 19.5 | 11.5 | 9.7 | 6.5 | 5.9 | 4.9 | 4.8 | 3.9 |

The anhydrate may be prepared by heating 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt or its derived monohydrate in an organic solvent or a mixture thereof with an aprotic co-solvent, such as isopropanol, dimethylsulfoxide, n-propanol, tetrahydrofuran or n-butanol, preferably n-butanol or tetrahydrofuran/n-butanol, to reflux or to a temperature between about 70° C. to about 90° C., preferably about 85° C. Depending on the reaction temperature and other conditions, the reaction time generally ranges from about 1 hour to about 20 hours, preferably about 2 hours to about 16 hours.

The crystal slurry formed is cooled to a temperature between about 20° C. to about 30° C., preferably about 25° C., for a time period between about 2 hours to about 24 hours, preferably about 2 hours to about 12 hours. The crystalline product is then filtered from the mother liquid and dried under vacuum until all the solvent has been removed.

The anhydrate may be administered as an antibacterial agent as described in above-mentioned U.S. Pat. No. 5,229,396. Administration to a subject may be alone, but the anhydrate will generally be administered in admixture with a pharmaceutical carrier selected with regard to the intended route of administration and standard pharmaceutical practice. For example, it can be administered orally or in the form of tablets containing such excipients as starch or lactose, or in capsules either alone or in admixture with excipients, or in the form of elixirs or suspensions containing flavoring or coloring agents. In the case of animals, it is advantageously contained in an animal feed.

| Peak no. | 1 | 2 | 3 | 4 | 5 | 6 | 7 | 8 | 9 | 10 |
|---|---|---|---|---|---|---|---|---|---|---|
| 2θ(°) Cu | 5.0 | 9.8 | 13.0 | 14.8 | 19.7 | 20.9 | 22.0 | 23.0 | 28.1 | 29.3 |
| d space | 17.9 | 9.0 | 6.8 | 6.0 | 4.5 | 4.2 | 4.0 | 3.9 | 3.2 | 3.0 |

The invention also provides pharmaceutical compositions comprising an antibacterially effective amount of the anhydrate together with a pharmaceutically acceptable diluent or carrier.

The anhydrate can be administered to humans for the treatment of bacterial diseases by either the oral or parenteral routes, and may be administered orally at dosage levels of about 0.1 to 500 mg/kg/day, advantageously 0.5–50 mg/kg/day given in a single dose or up to 3 divided doses. For intramuscular or intravenous administration, dosage levels are about 0.1–200 mg/kg/day, advantageously 0.5–50 mg/kg/day. While intramuscular administration may be a single dose or up to 3 divided doses, intravenous administration can include a continuous drip. Variations will necessarily occur depending on the weight and condition of the subject being treated and the particular route of administration chosen as will be known to those skilled in the art.

The antibacterial activity of the anhydrate is shown by testing according to the Steers replicator technique which is a standard in vitro bacterial testing method described by E. Steers et al., Antibiotics and Chemotherapy, 9, 307 (1959).

The hydration properties were determined gravimetrically over a range of relative humidities using a VTI microbalance system for moisture sorption studies (Model MB300W).

PREPARATION A 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt 7-([1α,5α,6α]-6-tert-butyloxycarbonylamino-3-azabicyclo[3.1.0]hex-3yl)-6-fluoro-1(2,4-difluorophenyl)-1,4-dihydro-4-oxo-1,8-naphthyridine-3-carboxylic acid, ethyl ester, (25 g) and methanesulfonic acid (11 g) was added to a mixture of water (250 mL) and tetrahydrofuran (250 mL). The resultant slurry was heated to reflux (about 66° C.) temperature and held at this temperature for 20 hours after which time a clear solution was obtained. The solution was cooled to 35°–40° C. and concentrated under reduced pressure to about half its original volume. The resultant crystal slurry was cooled slowly to room temperature (about 20° C.) and then further stirred at 10° C. for 2 hours. The crystalline product 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt was isolated by filtration and washed with a mixture of tetrahydrofuran (12.5 mL) and water (12.5 mL). The crystals were dried under vacuum at 30°–35° until the residual water content of the crystals was below 0.2%. Yield 21.2 g, 90%.

The crystals of 7-([1α,5α,6α]-6-amino-3-azabicyclo[3.1.0]hex-3-yl)-6-fluoro- 1-(2,4-difluorophenyl)-1,4-dihydro-4-oxo-1,8-naphthyridine-3-carboxylic acid, methanesulfonic acid salt are characterized by the major peaks in the following X-ray powder diffraction pattern.

| Peak no. | 1 | 2 | 3 | 4 | 5 | 6 | 7 | 8 | 9 | 10 |
|---|---|---|---|---|---|---|---|---|---|---|
| 2θ(°) Cu | 5.0 | 9.8 | 13.0 | 14.8 | 19.7 | 20.9 | 22.0 | 23.0 | 28.1 | 29.3 |
| d space | 17.9 | 9.0 | 6.8 | 6.0 | 4.5 | 4.2 | 4.0 | 3.9 | 3.2 | 3.0 |

The crystals of 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt can pick up water from the atmosphere and form a monohydrate. The monohydrate is characterized by the major peaks in the following X-ray powder diffraction pattern.

| Peak no. | 1 | 2 | 3 | 4 | 5 | 6 | 7 | 8 |
|---|---|---|---|---|---|---|---|---|
| 2θ(°) Cu | 4.7 | 9.4 | 12.4 | 13.1 | 13.6 | 14.2 | 17.0 | 17.9 |
| d space | 18.7 | 9.4 | 7.1 | 6.7 | 6.5 | 6.3 | 5.2 | 5.0 |
| Peak no. | 9 | 10 | 11 | 12 | 12 | 14 | 15 | |
| 2θ(°) Cu | 18.7 | 21.0 | 22.0 | 24.2 | 24.2 | 26.6 | 27.2 | |
| d space | 4.7 | 42 | 4.0 | 3.7 | 3.7 | 3.5 | 3.3 | |

EXAMPLE 1

7-([1α,5α,6α]-6-amino-3-azabicyclo[3.1.0]hex-3y)-6-fluoro-1-(2,4-difluorophenyl)-1,4-dihydro-4-oxo-1,8-naphthyridine-3-carboxylic acid, methanesulfonic acid salt, anhydrous 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt or its monohydrate (20 g) was stirred with isopropanol (220 ml). The crystal suspension was refluxed for 16 hours or until microscopic examination had shown that the crystal form had changed to a hexagonal form. The crystal slurry was cooled to 20°–25° C. and stirred at this temperature for about 1 hour. The crystalline product was filtered from the mother liquor, washed with isopropanol (about 50 mL) and dried under vacuum at 40° C. until all the solvent had been removed. Yield 98%.

The product is a new polymorphic form of 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt, anhydrous, characterized by the following major peaks in its X-ray powder diffraction pattern.

| Peak no. | 1 | 2 | 3 | 4 | 5 | 6 | 7 | 8 |
|---|---|---|---|---|---|---|---|---|
| 2θ(°)Cu | 4.5 | 7.7 | 9.1 | 13.6 | 15.0 | 18.2 | 18.6 | 22.8 |
| d space | 19.5 | 11.5 | 9.7 | 6.5 | 5.9 | 4.9 | 4.8 | 3.9 |

EXAMPLE 2

7-([1α,5α,6α]-6-amino-3-azabicyclo[3.1.0]hex-3y)-6-fluoro-1-(2,4-difluorophenyl)-1,4-dihydro-4-oxo-1,8-naphthyridine-3-carboxylic acid, methanesulfonic acid salt, anhydrous 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt or its monohydrate (7 g) was dissolved in dimethylsulfoxide, DMSO (21 mL) by heating to 80°–85° C. until complete solution was obtained. Isopropanol (150 mL) was added dropwise to the solution at about 85° C. to induce crystallization. The crystal suspension was held at reflux temperature about 85° C. for 2–16 hours or until microscopic examination had shown that the crystal form had changed to a hexagonal form. The resultant crystal slurry was cooled to 20°–25° C. The crystalline product was filtered from the mother liquor, washed with isopropanol (about 50 mL) and dried under vacuum at 50° C. until all the solvents had been removed. Yield 77%.

The product is the same as in Example 1.

EXAMPLE 3

7-([1α,5α,6α]-6-amino-3-azabicyclo[3.1.0]hex-3y)-6-fluoro-1-(2,4-difluorophenyl)-1,4-dihydro-4-oxo-1,8-naphthyridine-3-carboxylic acid, methanesulfonic acid salt, anhydrous 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt or its monohydrate (55.6 g) was dissolved in dimethylsulfoxide, DMSO (159 mL) by heating to 80°–85° C. until complete solution was obtained. The solution was cooled to 20°–25° C. and stirred for 2 hours until a crystal slurry formed. Dichloromethane (1200 mL) was added dropwise to the solution at about 25° C. to fully induce crystallization. The crystal suspension was held at room temperature overnight or until microscopic examination had shown that the crystal form had changed to a hexagonal form. The crystalline product was filtered from the mother liquor, washed with dichloromethane (3×119 mL) and dried under vacuum at 50° C. until all the solvent had been removed. Yield 91%.

The product is the same as in Example 1.

EXAMPLE 4

7-([1α,5α,6α]-6-amino-3-azabicyclo[3.1.0]hex-3y)-6-fluoro-1-(2,4-difluorophenyl)-1,4-dihydro-4-oxo-1,8-naphthyridine-3-carboxylic acid, methanesulfonic acid salt, anhydrous 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt or its monohydrate (1 g) was stirred with n-propanol (44 mL). The crystal suspension was refluxed for 3 hours or until microscopic examination had shown that the crystal form had changed to a hexagonal form. The crystal slurry was cooled at 20°–25° C. and stirred overnight. The crystalline product was filtered from the mother liquor, washed with n-propanol (about 10 mL) and dried under vacuum at 50°–55° C. until all the solvent had been removed. Yield 68%.

The product is the same as in Example 1.

EXAMPLE 5

7-([1α,5α,6α]-6-amino-3-azabicyclo[3.1.0]hex-3y)-6-fluoro-1-(2,4-difluorophenyl)-1,4-dihydro-4-oxo-1,8-naphthyridine-3-carboxylic acid, methanesulfonic acid salt, anhydrous 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt or its monohydrate (70 g) was stirred with a mixture of tetrahydrofuran (175 mL) and a n-butanol (525 mL). The crystal suspension was heated for 16 hours or until microscopic examination had shown that the crystal form had changed to a hexagonal form. The crystal slurry was cooled to 20°–25° C. and stirred overnight. The crystalline product was filtered from the mother liquor, washed with a mixture of tetrahydrofuran (25 mL) and n-butanol (75 mL) and dried under vacuum at 80° C. until all the solvent had been removed. Yield 95%.

The product is the same as in Example 1.

EXAMPLE 6

7-([1α,5α,6α]-6-amino-3-azabicyclo[3.1.0]hex-3y)-6-fluoro-1-(2,4-difluorophenyl)-1,4-dihydro-4-oxo-1,8-naphthyridine-3-carboxylic acid, methanesulfonic acid salt, anhydrous 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt or its monohydrate (5 g) was stirred with n-butanol containing up to 1% water (220 mL). The crystal suspension was heated to reflux for 5 hours or until microscopic examination had shown that the crystal form had changed to a hexagonal form. The crystal slurry was cooled to 20°–25° C. and stirred overnight. The crystalline product was filtered from the mother liquor, washed with n-butanol (about 20 mL) and dried under vacuum at 50°–55° C. until all the solvent had been removed. Yield 92%.

The product is the same as in Example 1.

We claim:

1. 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt characterized by the following major peaks in its X-ray powder diffraction pattern

| Peak no. | 1 | 2 | 3 | 4 | 5 | 6 | 7 | 8 |
|---|---|---|---|---|---|---|---|---|
| 2θ(°) Cu | 4.5 | 7.7 | 9.1 | 13.6 | 15.0 | 18.2 | 18.6 | 22.8 |
| d space | 19.5 | 11.5 | 9.7 | 6.5 | 5.9 | 4.9 | 4.8 | 3.9 |

2. A process for preparing the compound according to claim 1, which comprises heating 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt or its derived monohydrate in the presence of an alcohol or mixture thereof with an aprotic co-solvent.

3. A pharmaceutical composition having antibacterial activity, which comprises crystalline 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt characterized by the following major peaks in its X-ray powder diffraction pattern

| Peak no. | 1 | 2 | 3 | 4 | 5 | 6 | 7 | 8 |
|---|---|---|---|---|---|---|---|---|
| 2θ(°) Cu | 4.5 | 7.7 | 9.1 | 13.6 | 15.0 | 18.2 | 18.6 | 22.8 |
| d space | 19.5 | 11.5 | 9.7 | 6.5 | 5.9 | 4.9 | 4.8 | 3.9 |

4. A method of treating a bacterial infection, which comprises administering to a subject in need of treatment an antibacterial amount of crystalline 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt characterized by the following major peaks in its X-ray powder diffraction pattern

| Peak no. | 1 | 2 | 3 | 4 | 5 | 6 | 7 | 8 |
|---|---|---|---|---|---|---|---|---|
| 2θ(°) Cu | 4.5 | 7.7 | 9.1 | 13.6 | 15.0 | 18.2 | 18.6 | 22.8 |
| d space | 19.5 | 11.5 | 9.7 | 6.5 | 5.9 | 4.9 | 4.8 | 3.9 |

* * * * *